United States Patent [19]

Norris et al.

[11] Patent Number: 4,570,626
[45] Date of Patent: Feb. 18, 1986

[54] CORNEAL LIGHT SHIELD

[76] Inventors: John L. Norris, 70 Paseo Mirasol, Tiburon, Calif. 94920; Lee K. Schwartz, 50 Corte del Bayo, Larkspur, Calif. 94939

[21] Appl. No.: 572,284

[22] Filed: Jan. 20, 1984

[51] Int. Cl.⁴ ................................................ A61F 9/00
[52] U.S. Cl. .................................. 128/132 R; 128/163
[58] Field of Search ............ 128/132 R, 132 D, 25 A, 128/163; D24/66; 54/80; 351/177, 178, 247; 294/1.2; 2/15

[56] References Cited

U.S. PATENT DOCUMENTS

| | | | |
|---|---|---|---|
| 2,379,629 | 7/1945 | Eweson | 294/1.2 |
| 3,973,561 | 8/1976 | Kane | 128/132 R |
| 4,122,847 | 10/1978 | Craig | 128/132 R |

FOREIGN PATENT DOCUMENTS 2001778  2/1979  United Kingdom ................ 294/1.2

Primary Examiner—Gene Mancene
Assistant Examiner—John G. Weiss
Attorney, Agent, or Firm—Townsend and Townsend

[57] ABSTRACT

This invention provides apparatus and method for preventing eye damage, particularly to the retina, resulting from direct exposure of the eye to intense light from a light source during eye surgery. A shield having a diameter less than that of the cornea is placed directly on the cornea, between the light source and the retina. By so doing, this shield prevents damage to the eye, and especially to the retina, to thereby enhance probability and speed of full recovery after eye surgery.

12 Claims, 4 Drawing Figures

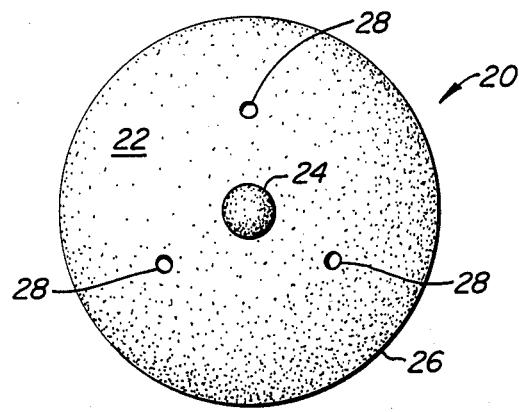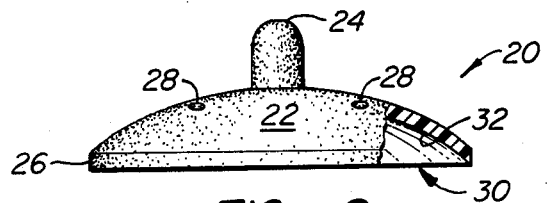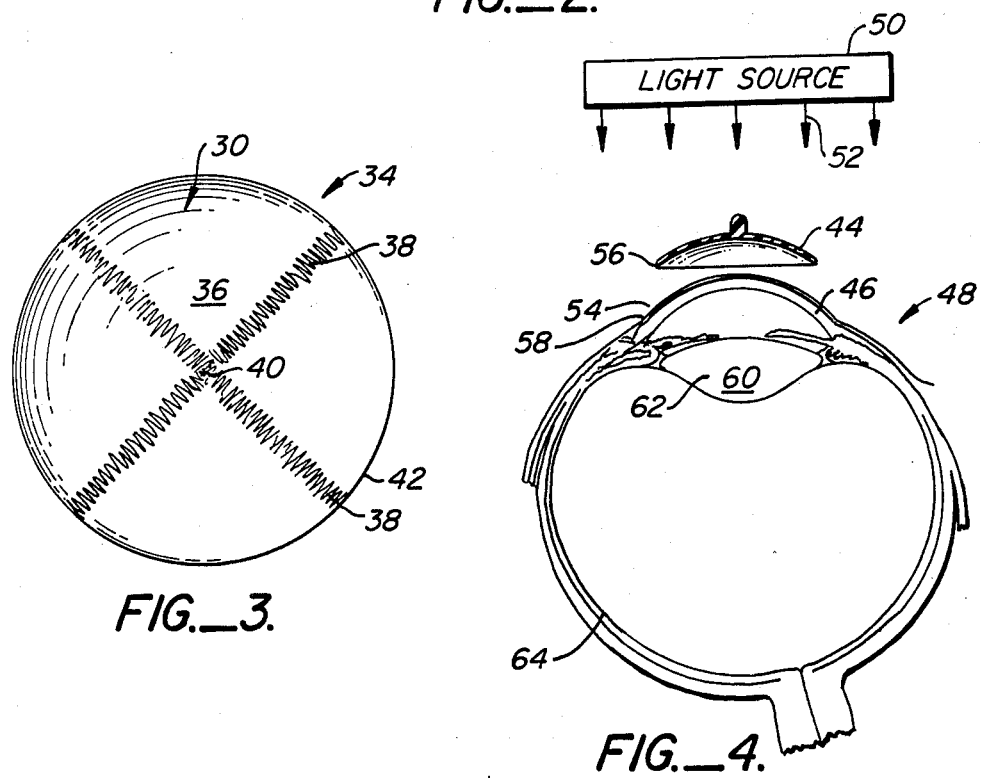

CORNEAL LIGHT SHIELD

BACKGROUND OF THE INVENTION

1. Field of the Invention

This invention relates generally to means for protecting an eye during surgery, and more particularly to techniques for shielding the retina from damaging high energy light during eye surgery.

2. Description of the Prior Art

Many kinds of eye surgery benefit from covering the eye during at least a portion of the operation. Cataract surgery is an example. A cataract is a clouding which occurs in the crystalline lens or lens capsule, which obstructs light passage.

Surgical techniques exist for the removal of cataracts from the eye. If the cataracts are severe enough, the original natural lens can be removed and replaced with a substitute intraocular lens. An incision is made at the junction (i.e., the limbus) of the cornea with the remainder of the eyeball, which is covered with a tough coating (i.e., the sclera) over the remainder of the eye. The cataract can be totally removed by applying a cryoprobe (freezing). Alternatively, the cataract can be removed by opening the anterior lens capsule; the nucleus of the cataract can then be manipulated out by a conventional pressure-counter pressure technique, or by use of a hollow vacuum pump-operated aspiration needle with ultrasound attachment to break up the nucleus into fine pieces that will fit through the needle. The cataract is then sucked out in the same manner as a vacuum cleaner operates.

A light source is used to provide light for illuminating the anterior segment of the eye upon which surgery is being performed. Best lighting is achieved by directing the light beam substantially perpendicular to the cornea. Disadvantages, however, exist with present lighting techniques. It is believed that intense and prolonged exposure of the retina to the light source may cause delay in recovery of the visual acuity of the eye. Further, it is suspected that present lighting techniques may cause permanent eye damage which sometimes results from eye surgery using a conventional operating microscope.

Attempts have been made to attenuate light received by the retina. One approach uses side lighting; several light sources are placed around the periphery of the eye, to shine in through the cornea toward the lens at an angle away from the perpendicular to the cornea. However, side lighting has the significant disadvantage of interfering shadows being cast by the surgeon's fingers, hands and instruments as all are moved during surgery. These shadows interfere with the vision of the surgeon.

Another attempted solution has been to place filters between the light source and eye. However, it is not known exactly which filters are required to prevent retina injury.

Protective shields for placing directly on the eyeball have been devised for use in plastic surgery. The eyeball is totally covered with the opaque shield to protect it from injury while surgery is performed on eye lids. However, the shield is not used for eye surgery because it totally obscures those regions of the eyeball upon which an operation is to be performed.

SUMMARY OF THE INVENTION

This invention provides a novel apparatus and method for preventing retina damage resulting from direct exposure to intense light during eye surgery using an operating microscope. In particular, the invention comprises a shield for emplacement over the cornea, the shield being complementary in shape to the cornea.

The opaque disc-shaped shield has a diameter less than the diameter of the cornea. This permits use of a light beam substantially perpendicular to the cornea and having a diameter greater than the diameter of the cornea. The shield, by removing the central portion of the beam, reduces damage to the retina. The shield can be used in any eye surgery to prevent damage to the cornea and to prevent light injury to the retina, two examples being cataract surgery and retinal reattachment surgery.

Further, by placing the shield directly onto the cornea, the cornea remains moist throughout the surgery, and does not dry out in the manner typical of the previous techniques used. Also, the shield is made of a material which can absorb impact during surgery. One embodiment includes a knob affixed to the external surface of the shield, for moving the shield around on and away from and toward the cornea.

BRIEF DESCRIPTION OF THE DRAWINGS

FIG. 1 is a top view according to a first embodiment of the invention;

FIG. 2 is a side view of the FIG. 1 embodiment;

FIG. 3 is a bottom view of the invention according to a second embodiment of the invention; and FIG. 4 is a side view of the invention during use on an eye.

DETAILED DESCRIPTION OF PREFERRED EMBODIMENTS

FIG. 1 and FIG. 2 show that shield 20 is a cup-shaped disc including an upwardly convex top surface 22, which at its peak is provided with a knob 24, useful for gripping by forceps (not shown) for lifting and moving of shield 20.

An interior chamber 30 is defined by the interior concave surface 32 within shield 20. Chamber 30 is designed for concave surface 32 to sit on and conform to the outer convex surface of the cornea during surgery. Shield 20 is fabricated to be opaque. The shield can be fabricated from a hard material such as polymethylmethacrylate, or from a flexible material such as silicone.

Approximately halfway between rim 26 and knob 24 are holes 28, positioned 120° apart from one another around the surface 22. Holes 28 provide an air passageway, permitting atmospheric air to come into contact with the surface of the cornea (see FIG. 4), to thereby eliminate suction.

FIG. 3 is a second embodiment of the invention when viewed from the bottom. To prevent suction, the shield's concave surface 36 has radial serrations 38, extending from a concave peak 40 outward toward rim 42. Atmospheric air migrates between concave surface 36 and the cornea by traveling along serrations 38.

FIG. 4 is a side view of a shield 44 (of either the FIGS. 1 and 2, or FIG. 3 embodiments), above a cornea 46 of an eye 48. Cornea 46 has a linear diameter ranging from 12 to 13 millimeters when viewed from the top.

Thus when a light source 50 sends out light 52, shield 44 absorbs light 52 except where the light is able to pass through the region 54 existing between the rim 56 of the shield 44 and cornea rim 58. This permits a cylinder of light to illuminate the peripheral cornea but blocks light to the pupillary opening.

The diameter of shield 44 ranges from 4 to 13 millimeters, depending on the diameter of the cornea and the pupillary opening within the eye permitting light to pass into an eye's crystalline lens 60. However, experimentation has shown that a diameter of 10 millimeters provides optimum eye protection while still admitting sufficient light to perform surgery.

It is within lens 60 that opacities are found that are called cataracts. Sufficient light is reflected from mirrors (not shown), used in cooperation with light source 50, to direct light 52 toward the surgical area. Sometimes only the cataracts are removed. However, if the cataracts are severe enough, the original natural lens can be removed and replaced with a substitute lens.

In use during surgery, shield 44 need not be placed on the cornea until after the cataract 62 has been removed from the eye, because light intensity is not a problem for the retina until after the cataracts are out of the way. However, as soon as the cataracts 62 have been removed, shield 44 is placed onto cornea 46. This prevents any direct light 52 from reaching the pupillary opening and/or an intraocular lens implant for focusing to a damaging spotlight on the retina 64, thereby preventing damage to retina 64.

The elapsed time between the beginning of the surgery and emplacement of shield 44 on cornea 46 ranges from (1) 15 to 20 minutes for a very fast operation, for a total operating time of 25 minutes, up to (2) an hour and a half to two hours operating time if complications arise.

Most complications occur after the cataracts 62 have been removed. Therefore these complications tend to arise approximately 15 to 20 minutes into the surgery. However, at this point shield 44 is placed onto cornea 46, so the remedies for complications can be performed without exposing retina 64 to direct light 52. The surgeon can take as much time as necessary to correct the complications, without worrying about damage to the retina.

Because shield 44 has a diameter smaller than cornea 46, the incision made at the inception of the surgery can be sutured around the cornea rim 58 while shield 44 is in place against cornea 46. Additionally, because shield 44 is in constant contact with cornea 46, the cornea is kept moist throughout the remainder of the operation after the cataract has been removed. Shield 44 is impact resistant to absorb mechanical shocks inadvertently delivered to the shield which would otherwise pass on to and possibly damage the eye 48.

While the above provides a full disclosure of the preferred embodiments of the invention, it will be apparent to those skilled in the art that various modifications, alternate constructions, and equivalents may be employed, without departing from the true spirit and scope of the invention. The scope of the invention shall be defined by the breadth of the appended claims.

What is claimed is:

1. An apparatus for preventing high intensity light burns to the retina of an eye during the illumination and surgery on the eye, the apparatus comprising an opaque shield of diameter less than the diameter of the cornea of the operated upon eye, the shield having a concave contour disposed toward and complementary in shape to the cornea for resting thereon.

2. The apparatus of claim 1, further including means for manipulating the shield with respect to the cornea.

3. The apparatus of claim 1, wherein the shield is comprised of a resilient material.

4. The apparatus of claim 1, wherein the shield is fabricated from flexible silicone.

5. The apparatus of claim 1, wherein the shield is fabricated from a hard material.

6. The apparatus of claim 1, wherein the shield is fabricated from hard polymethylmethacrylate.

7. The apparatus of claim 1, wherein the shield is a disc having a diameter ranging from 4 to 13 millimeters.

8. The apparatus of claim 1, wherein the shield is constructed of shock absorbent material to protect the eye from impact.

9. The apparatus of claim 1, further including means for eliminating suction when the shield is moved on or away from the cornea.

10. The apparatus of claim 9, wherein the means for eliminating suction comprises a hole provided through the shield, the hole providing fluid communication between the cornea and the atmosphere.

11. The apparatus of claim 9, wherein the means for eliminating suction comprises an inner surface including a serrated portion for providing fluid communication between the cornea and the atmosphere.

12. The method for protecting the retina of an eye from a light source during eye surgery on the protected eye, comprising the steps of:
    (a) sizing a shield to have a diameter less than that of a cornea;
    (b) contouring the shield to be complementary to the shape of the cornea;
    (c) placing the shield on the outside surface of the cornea; and
    (d) maintaining the shield against the cornea during at least a portion of the surgery.

* * * * *